United States Patent
Samuelson et al.

(10) Patent No.: US 8,492,117 B2
(45) Date of Patent: Jul. 23, 2013

(54) EXPRESSION OF TOXIC GENES IN VIVO IN A NON-NATURAL HOST

(75) Inventors: James C. Samuelson, Newburyport, MA (US); Theodore B. Davis, Boxford, MA (US); Elisabeth A. Raleigh, Somerville, MA (US); Maurice W. Southworth, Newburyport, MA (US)

(73) Assignee: New England Biolabs, Inc., Ipswich, MA (US)

( * ) Notice: Subject to any disclaimer, the term of this patent is extended or adjusted under 35 U.S.C. 154(b) by 805 days.

(21) Appl. No.: 12/517,580

(22) PCT Filed: Dec. 3, 2007

(86) PCT No.: PCT/US2007/086274
§ 371 (c)(1),
(2), (4) Date: Jan. 5, 2010

(87) PCT Pub. No.: WO2008/073746
PCT Pub. Date: Jun. 19, 2008

(65) Prior Publication Data
US 2010/0129916 A1    May 27, 2010

Related U.S. Application Data

(60) Provisional application No. 60/873,711, filed on Dec. 8, 2006, provisional application No. 60/959,322, filed on Jul. 12, 2007.

(51) Int. Cl.
*C12P 21/02*    (2006.01)

(52) U.S. Cl.
USPC ............... 435/69.1; 435/252.33; 435/235.1; 435/320.1

(58) Field of Classification Search
None
See application file for complete search history.

(56) References Cited

U.S. PATENT DOCUMENTS

| | | |
|---|---|---|
| 4,952,496 A | 8/1990 | Studier et al. |
| 5,824,528 A | 10/1998 | Studier et al. |
| 5,830,694 A | 11/1998 | Studier et al. |
| 6,569,669 B1 | 5/2003 | Raleigh |

OTHER PUBLICATIONS

Kang, et al., Abst. Gen. Meet. ASM, 106:293 (2006).
International Search Report for PCT/US2007/086274, mailed Aug. 5, 2008.

*Primary Examiner* — Jim Ketter
(74) *Attorney, Agent, or Firm* — New England Biolabs, Inc; Harriet M. Strimpel

(57) ABSTRACT

Compositions and methods are provided for expression of a toxic protein in a host cell preferably a bacterial host cell where at least one T7 RNA polymerase gene Is contained on the host cell chromosome and one or more genes encoding a T7 RNA polymerase inhibitor is located on an F' plasmid or on the chromosome.

16 Claims, 13 Drawing Sheets

SEQUENCE LISTING

<160> NUMBER OF SEQ ID NOS: 3

<210> SEQ ID NO 1
<211> LENGTH: 38
<212> TYPE: DNA
<213> ORGANISM: artificial

```
<220> FEATURE:
<223> OTHER INFORMATION: primer

<400> SEQUENCE: 1
ccaccagacg tcaccatcga atggtgcaaa acctttcg                               38

<210> SEQ ID NO 2
<211> LENGTH: 31
<212> TYPE: DNA
<213> ORGANISM: artificial
<220> FEATURE:
<223> OTHER INFORMATION: primer

<400> SEQUENCE: 2
atgataagac gtcaaacatg agaattgtgc c                                      31

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
gcttcctcgc tcactgactc                                                   20
```

EXPRESSION OF TOXIC GENES IN VIVO IN A NON-NATURAL HOST

CROSS REFERENCE

This application is a §371 application of international application number PCT/US2007/86274 filed on 03 Dec. 2007, which claims priority from U.S. provisional application number 60/873,711 filed on 8 Dec. 2006 and U.S. provisional application number 60/959,322 filed on 12 Jul. 2007, herein incorporated by reference.

BACKGROUND OF THE INVENTION

Toxic proteins are defined by their negative effect on cell viability and therefore cloning and expressing of such toxic genes have proved problematic. One approach to this problem has been to generate cell-based expression systems that are inducible. The theory is that gene expression is inhibited in host cells until the cell density has reached the desired concentration at which time the inhibition of protein expression is reversed and protein is expressed up to a threshold amount before viability is compromised.

An example of an inducible cell system is BL21(DE3), This is an *E. coli* host strain in which the bacteriophage DE3, which is a lambda derivative, has been incorporated into the host cell chromosome, the DE3 prophage encodes the gene for T7 RNA polymerase, which is regulated by the lacUV5 promoter and controlled by LacI repression (U.S. Pat. No. 4,952,496). In such DE3 lysogens, the target gene is typically expressed from a multi-copy plasmid by transcription from a T7 promoter. Thus, induction of target gene expression can be activated by IPTG or allolactose. Unfortunately this system permits a significant amount of basal expression of toxic protein under LacI repression and therefore significantly compromises clone stability and yield of protein.

Various attempts have been mode to reduce basal expression, (See for example, Dubendorff and Studier, *J. Mol. Biol.* 219:45-59 (1991); Moffatt and Studier, *Cell* 49:221-227 (1987); Studier *J. Mol. Biol.* 219:37-44 (1991)). These modifications include expressing the target gene from a T7-lac promoter. The T7-lac promoter consists of a lac operator sequence inserted just downstream of the T7 φ10 promoter (beginning with vector pET-10). This enables the Lac repressor to bind at the transcriptional start site and function to reduce transcription in the absence of induction. In such T7 lac vectors, the vector also encodes lacI to provide a greater supply of Lac repressor.

Another modification is the introduction of a multi-copy plasmid that contains a gene expressing an inhibitor of the T7 RNA polymerase, in particular, wild type (WT) T7 lysozyme (pLysS, pLysE, pLysL, and pLysH). In pLysS and pLysL, lysozyme expression is constitutively expressed by readthrough transcription from the CAT promoter. In pLysE and pLysH, lysozyme is expressed at a higher level from the tet promoter.

U.S. Pat. No 6,569,669 describes a host cell with an increased concentration of lac repressor (greater than about 10 molecules per cell) to control the expression of a foreign RNA polymerase.

The above attempted solutions have some disadvantages. These include the following:

(a) Even when it is desirable to induce target gene expression, the constitutive production of T7 lysozyme from multi-copy plasmids results in a lag time after induction before a sufficient level of T7 RNA polymerase is produced to effect gene expression. This is especially significant when using pLysE for expression of extremely toxic genes. This expression lag is problematic because there is a limited window of maximal protein production during the exponential growth phase of a typical fermentation.

(b) Maintenance of the multi-copy plasmids requires the addition of chloramphenicol (CAM) into the growth media of the host cells that results in significant expense for large-scale fermentations.

(c) The second multi-copy plasmid may interfere with the characterization of the multi-copy plasmid expressing the target protein from the host cells.

(d) The expression of large amounts of secondary proteins from the multi-copy plasmids (such as lysozyme and antibiotic resistance proteins, e.g. CAT) puts a burden on the protein translation apparatus that might otherwise make larger amounts of the target protein.

(e) The expression of active T7 lysozyme within a protein expression strain may also interfere with post expression cell processing and with certain experimental procedures. For example, pLysS and pLysE strains often lyse spontaneously upon freezing and thawing.

(f) The co-expression of active T7 lysozyme during target membrane protein over-expression may result in cell lysis and a reduction in culture yield.

SUMMARY

In an embodiment of the invention, a genetically engineered host cell is provided that is capable of expressing a toxic protein. An example of a host cell is an *E. coli* host cell. The host cell contains a chromosome in which is incorporated one or more T7 RNA polymerase genes. The host cell additionally contains one or more genes encoding a T7 RNA polymerase inhibitor located in an F' plasmid or on the chromosome. The one or more T7 RNA polymerase genes may be present in a ratio of 1:1 with the one or more T7 RNA polymerase inhibitor genes. In addition to the one or more T7 RNA polymerase genes and the one or more T7 RNA polymerase inhibitor genes, the host cell may additionally contain a gene expressing LacI or LacIq. An example of a T7 RNA polymerase inhibitor gene is the T7 lysozyme gene where this gene may express a mutant T7 lysozyme. Examples of mutant T7 lysozymes are those which contain at east one of the following mutations: Y46F, K128Q, K128Y, K128M, K128W and K128I.

Another feature of the host cell is that it is competent for receiving foreign DNA.

In another embodiment of the invention, an F' plasmid is provided which contains a T7 lysozyme gene or modifications thereof operably linked to a constitutive promoter. The modified lysozyme gene expresses a mutant T7 lysozyme. In one example, the mutant T7 lyre has a K128Y mutation. In other examples, the lysozyme may have mutations selected from at least one of Y46F, K128Q, K128M, K128W and K128I.

In another embodiment of the invention, a method is provided that includes the steps of (a) providing a genetically engineered host cell of the type described above; (b) transforming the host cell with a plasmid containing a target gene; (c) incubating the host cell to a cell density sufficient to permit expression of the target gene; and (d) inhibiting the basal level of T7 RNA polymerase activity until initiation of induction so as to permit expression of the target gene in the genetically engineered host cell.

In additional embodiments, the target gene expresses a toxic protein such as a membrane protein. The T7 RNA polymerase inhibitor may be selected from a wild type or mutant lysozyme gene where the mutation may be one or more of the following mutations: Y46F, K128Q, K128Y, K128M, K128W and K128I.

Large amounts of CAT and lysozyme are shown in ER2566 cells transformed with pLysY (3), pLysE (4) or pLysY (5), whereas these bands were not observed in ER2833 (F'lacIq) or with ER2566 in which the lysozyme plasmids were absent.

Figure 5:
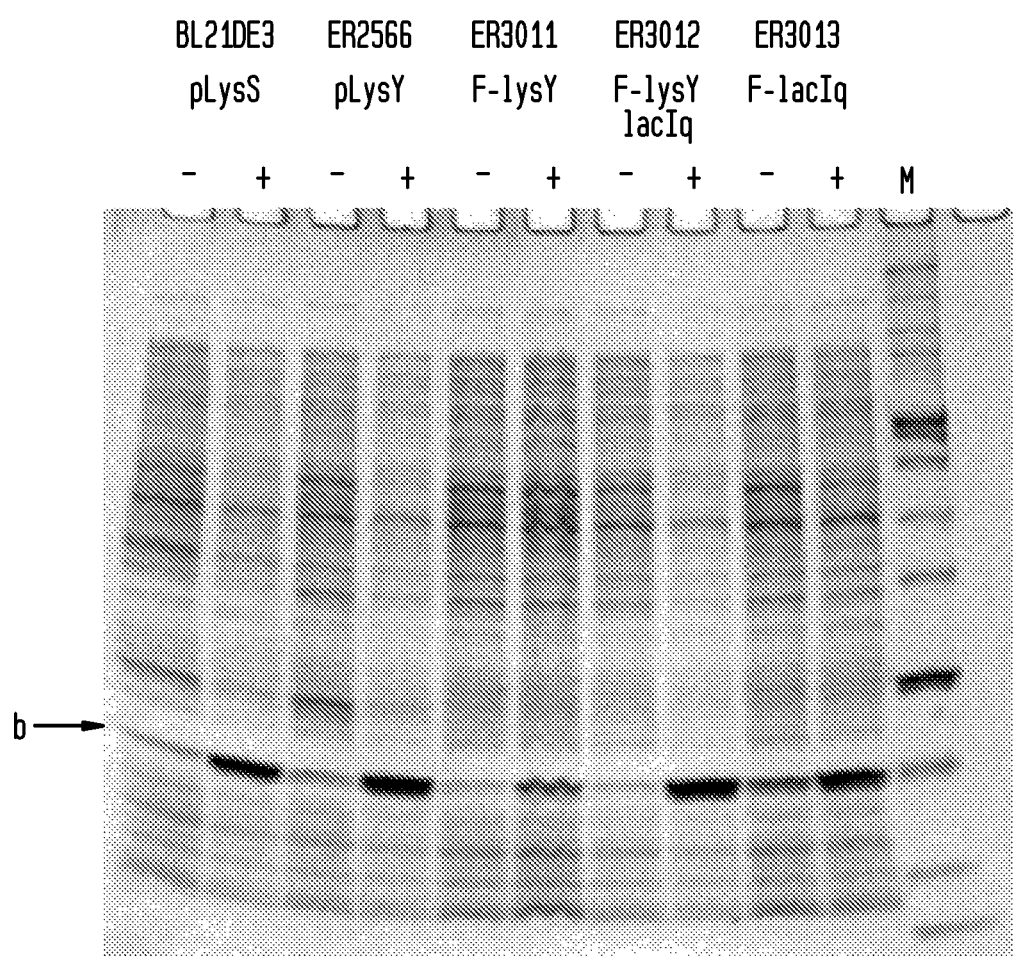

FIG. 5 shows an SDS-PAGE analysis of expression of a highly toxic protein identified as *E. coli* ATP synthase subunit b (uncF gene product) from a variety of inducible cell systems. Individual colonies were inoculated in 4 mL LB plus 100 µg/mL ampicillin (Amp) and grown overnight to saturation. 30 µg/mL Cam was added only to strains carrying pLysS or pLysY. These starter cultures were inoculated into the same respective media (1:100 dilution) to grow for expression of subunit bat 37° C. (−) no IPTG; (+) 0.5 mM IPTG induction for 3 hours. From the left of the gel, lanes 1 and 2 show expression of subunit b in BL21DE3 (pLysS), lanes 3 and 4 show expression of subunit bin ER2566 (pLysY), lanes 5 and 6 show expression of subunit b in ER3011 (F-lysY), lanes 7 and 8 show expression of subunit b in ER3012 (F-lysY-lacIq), lanes 9 and 10 show expression of subunit b in ER3013 F'-lacIq). Lane 11 is the marker.

Figure 6:
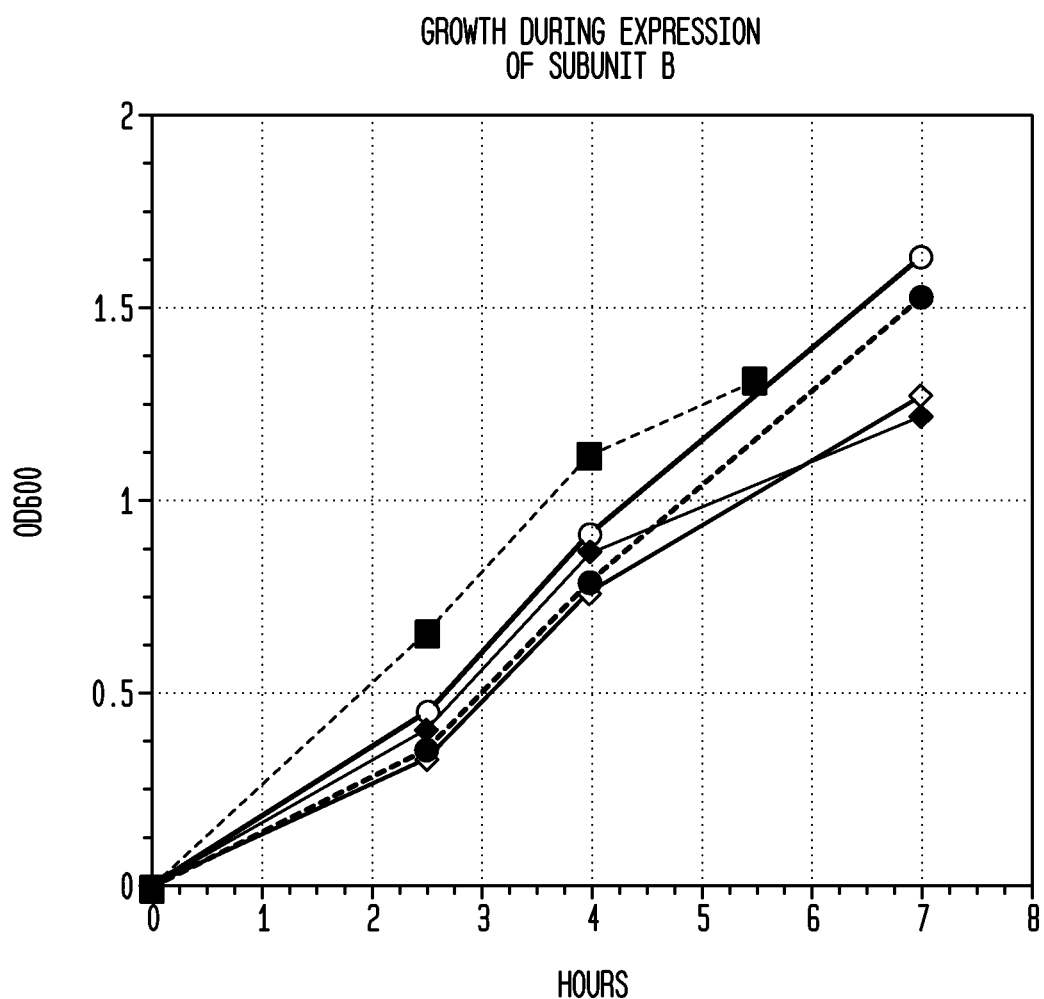

FIG. 6 shows growth rates at 37° C. of strains expressing subunit b. Cultures were grown as described in FIG. 5: The ER3012 strain expressing both LysY and LacIq achieved the point of induction 1.5 hours earlier than all other strains, thus allowing for culture harvest 1.5 hours earlier. ER3011 and ER3013 also outperformed the multi-copy lysozyme strains especially during the final 3-hour subunit b induction period.

FIG. 7 shows SDS-PAGE analysis of uracil DNA glycosylase (UDG) expression. A single colony transformant (pTYB-UDG) was inoculated into 5 mL SOB (plus 100 µg/mL Amp) and grown for 6 hours before induction of (+) cultures with 0.5 mM IPTG for 3 hours. The ER2566 Control Strain does not carry a UDG expression plasmid. BL21(DE3) early provides an excessive basal level of UDG expression.

Figure 7A:
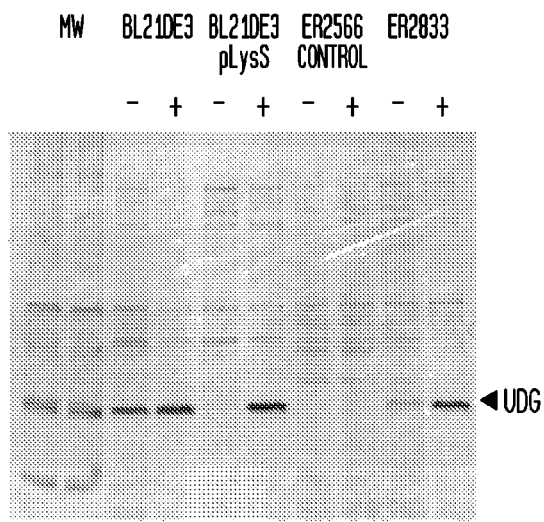

FIG. 7a: lanes 1 and 2 contain molecular weight markers. Expression of UDG by different host cells is shown in lanes 3-10. Lanes 3 and 4: BL21DE3 with no lysozyme gene, lanes 5 and 6: BL21DE3 (pLysS), lanes 7 and 8: ER2566 lacking a target gene, lanes 9 and 10: ER2833 (F'lacIq) with no lysozyme gene.

Figure 7B:
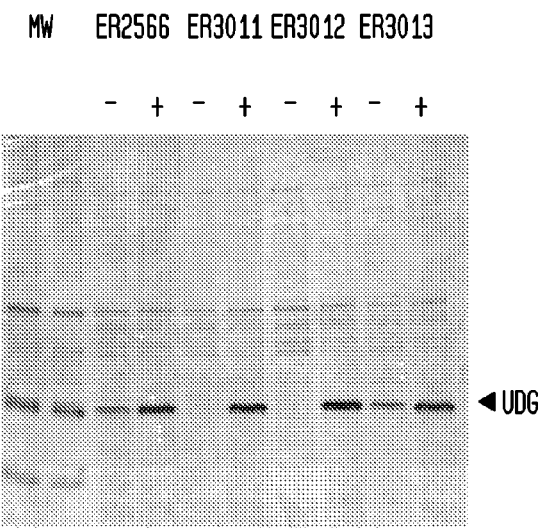

FIG. 7b: Lanes 1 and 2: markers; expression of UDG by different host cells is shown in lanes 3-10. Lanes 3 and 4; ER2566 (no lysozyme), lanes 5 and 6: ER3011 (miniF-lysY), lanes 7 and 8: ER3012 (miniF-lysY-lacIq), lanes 9 and 10 ER3013 (miniF-lacIq).

Figure 8:
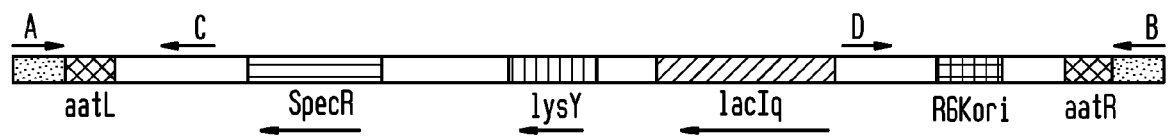

FIG. 8 is a diagram of the chromosomal insertion sequence in strains ER3043 and ER3044 (see Example 7). The shaded regions indicate the junction with *E. coli* chromosome. In these strains, lysozyme expression was accomplished by read-through from constitutive lacIq transcription. Uppercase letters A, B, C and D indicate PCR primers used to confirm the presence of the chromosomal insertion sequence.

Figure 9:
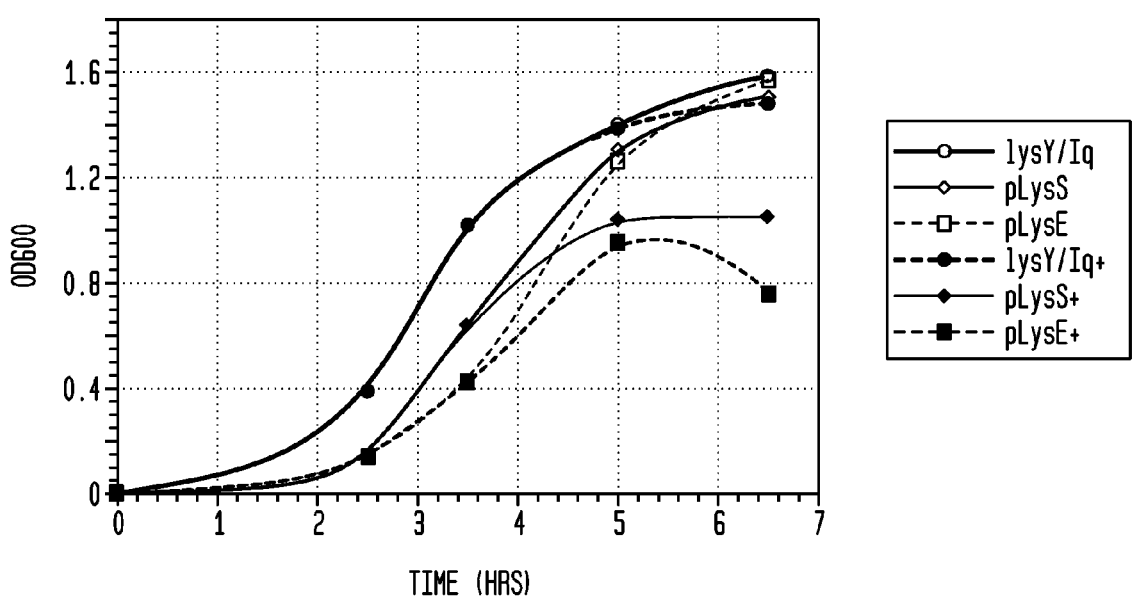

FIG. 9 shows that host cells encoding a single copy of the lysY gene (i.e., ER3012 lysY/Iq) were significantly less susceptible to cell lysis upon induction of a target membrane protein as compared to pLysS and pLysE strains expressing WT T7 lysozyme, ER301.2 achieved a much greater cell density upon induction of ATP synthase subunit b and the viable cell count was at least 100-fold greater after the induction period. This advantage resulted in a higher yield of cells and a higher yield of target protein. Note that two curves were plotted for each strain. (+) indicates the growth curves for the cultures induced with 0.5 mM IPTG for 3 hours. The induction period is from 3.5 to 6.5 hrs. The number of viable cells were measured after the 3-hr induction period where viable ER301.2 lysY/Iq=2.0×10$^8$/ml, viable BL21(DE3) pLysS=<2.0×10$^5$/ml and viable BL21(DE3)pLysE=1.2×10$^6$/ml.

Figure 10A:
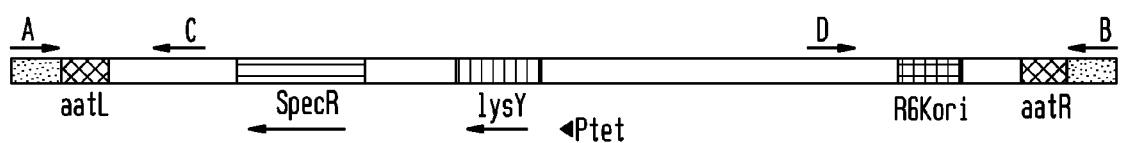

FIG. 10a shows the chromosomal insertion at the attB locus within strains ER3080 and ER3082 (see Example 8). ER3080 contains the lysY allele while ER3082 contains the WT T7 lysozyme gene (lysZ) on the chromosome. In both strains, the lysozyme gene was constitutively expressed from the Ptet promoter derived from pACYC184. Uppercase letters A, B, C and D indicate PCR primers used to confirm the presence of the chromosomal insertion sequence.

Figure 10B:
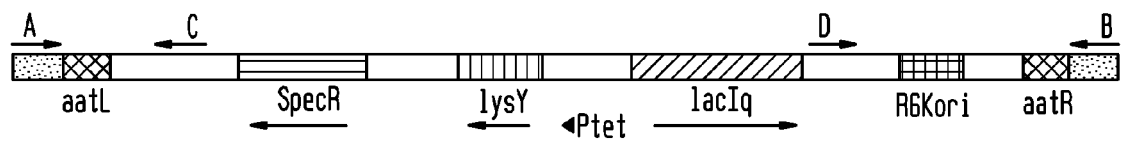

FIG. 10b shows the chromosomal insertion at the attB locus within strains ER3081 and ER3083 (see Example 8), ER3081 carries the lysY allele plus the lacIq gene. ER3083 carries the WT T7 lysozyme gene (lysZ) plus the lacIq gene. An important difference between the strains ER3043 and ER3044 and the strains ER3080, ER3081, ER3082 and ER3083 is that the lysozyme gene is constitutively expressed from the Ptet promoter derived from pACYC184. Uppercase letters A, B, C and D indicate PCR primers used to confirm the presence of the chromosomal insertion sequence.

Figure 11:
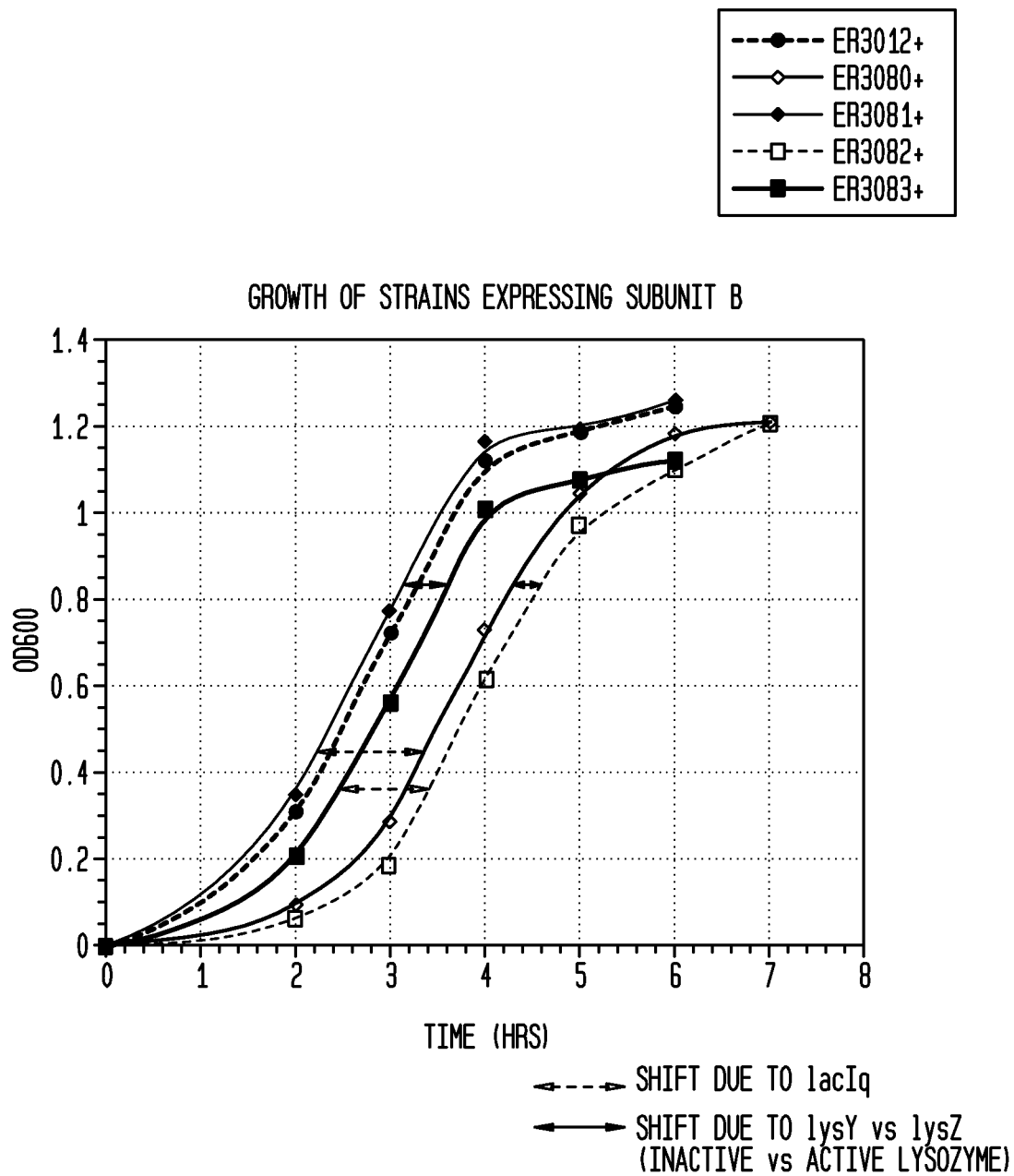
Figure 12:
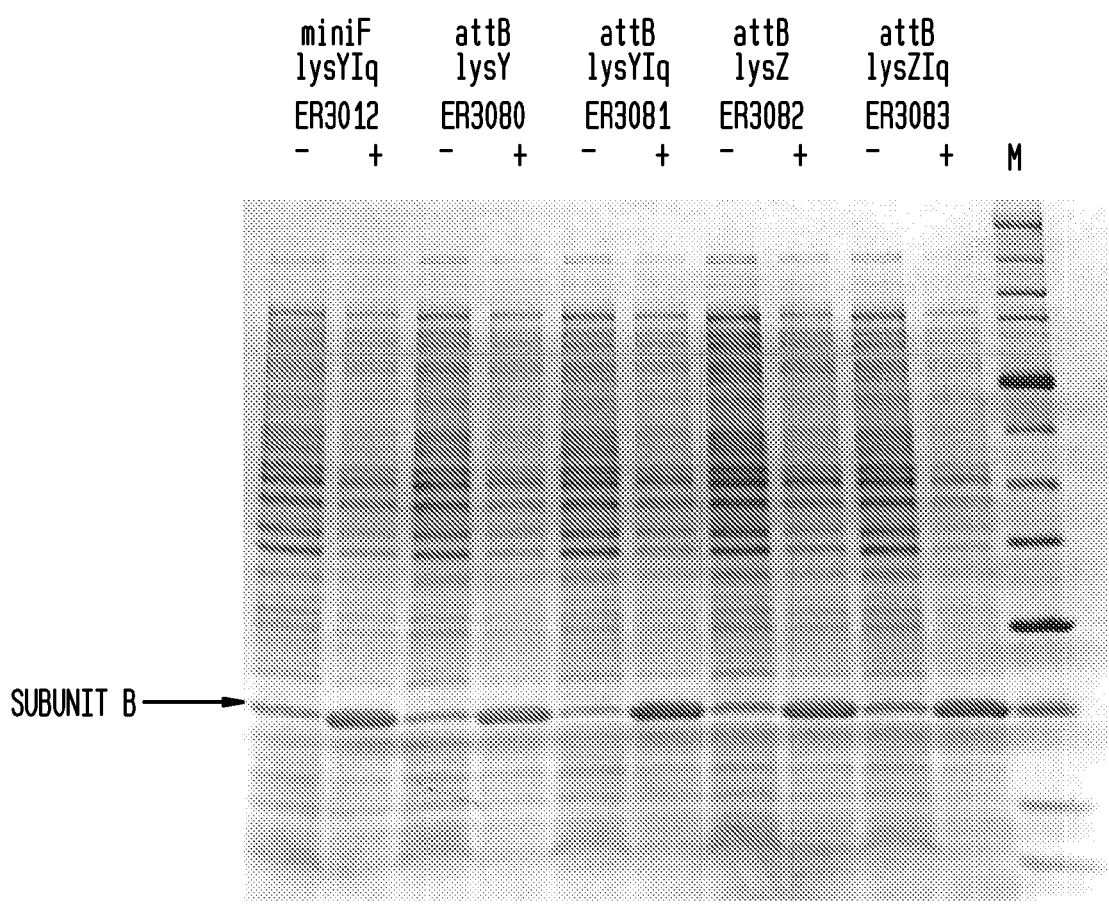

FIG. 11 shows the growth rates of four chromosomal T7 lysozyme strains compared to the miniF-lysY/Iq strain ER3012 during expression of subunit b. All strains were first grown overnight to saturation from a single colony at 37° C. in LB plus Amp. Then a 1:100 inoculation was made into LB plus ampicillin. The expression cultures were grown at 37° C. and the cell density was measured periodically at 600 nm. Protein expression was induced with 0.5 mM IPTG within the OD range 0.56-0.77. Three hours post-induction, samples were taken from minus IPTG (−) and plus IPTG (+) cultures for SDS-PAGE analysis (FIG. 12). All strains displayed favorable growth rates and there was no indication of culture lysis, LysY strains were. shown to have a growth advantage over LysZ strains (see ⇐⋯⇒ for shift due to LysY compared to lysZ), LacIq strains achieved the point of induction 1 hour earner than equivalent non-lacIq strains (see <- - -> for shift due to lacIq).

FIG. 12 shows a subunit b over-expression analysis of four chromosomal T7 lysozyme strains compared to the miniF-lysY/Iq strain ER3012. These four strains are ER3080 (attB::lysY), ER3081 (attB::lysYIq) and ER3082 (attB::lysZ) and ER3083 (attB::lysZIq) where attB denotes a single copy of T7 lysozyme expressed from the chromosome. Samples from the experiment described in FIG. 11 were analyzed by SDS-PAGE (10-20% acrylamide gradient gel). Each strain produced subunit b at a high level. In every case, at least a 10-fold ratio of induced protein to non-induced protein was observed. Note that subunit b was expressed from a plasmid (pAVD10) with a T7 promoter without a lac operator sequence or a lac repressor gene (lacI) and therefore any control of expression must come from the host cell itself.

Figure 13:
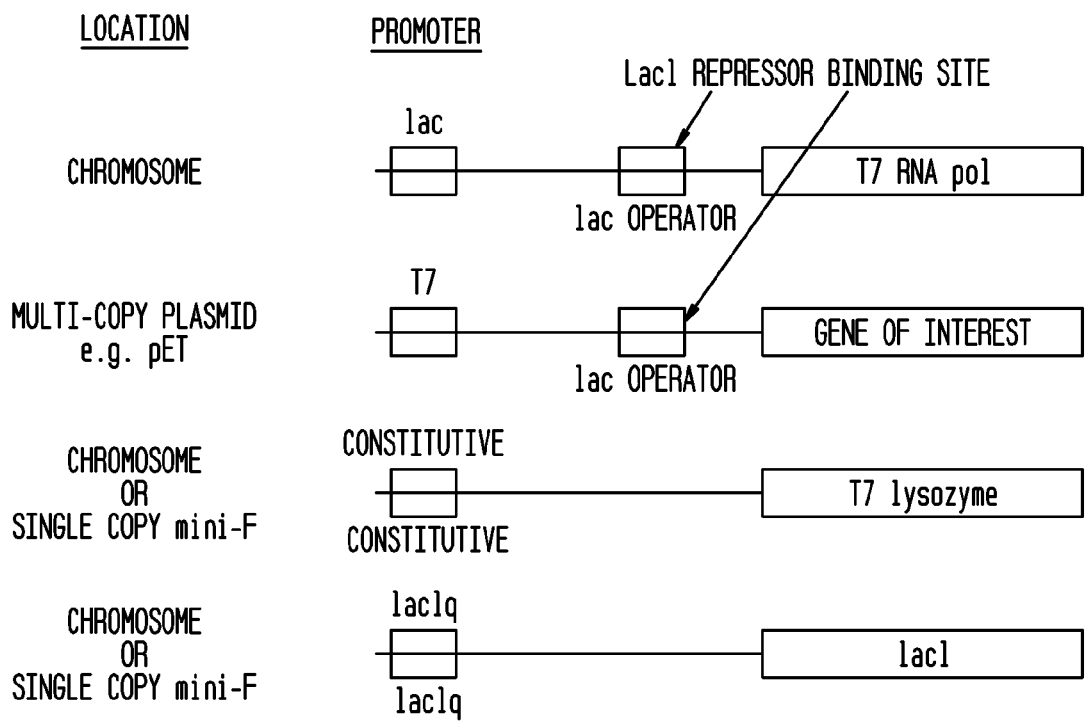

FIG. 13 shows the relevant features of the T7 expression systems within the strains of the present invention, M described host cells have the common feature of a T7 RNA polymerase gene in the chromosome within the lac locus. The T7 lysozyme gene may be present in one of two locations and is expressed from a constitutive promoter. The lacIq repressor gene may optionally be provided within one of two locations and is expressed from the lacIq promoter. The gene of interest is not provided within the host cells of the present invention as this is supplied by the end user.

DETAILED DESCRIPTION OF THE EMBODIMENTS

Present embodiments of the invention provide improved expression systems that overcome at least some of the disadvantages cited above.

In an embodiment of the invention, host cells with improved toxic protein production express both lacIq and a T7 lysozyme gene from the chromosome or from a stably maintained F plasmid. The improved strains contain a single copy of as gene encoding a T7 RNA polymerase inhibitor such as T7 lysozyme either on the chromosome or on an F' plasmid.

An advantage of chromosomal expression of both lacIq and T7 lysozyme is that antibiotics are not required to grow cells providing maximum flexibility for introducing vectors containing the target gene. The plasmid-free host cells have advantages that include the option by the end user to subsequently introduce any combination of compatible vectors. The use of this expression strain provides greater flexibility with respect to the choice of antibiotics for introducing the gene of interest or other plasmids into the cell.

An advantage of miniF plasmids (less than 10 kb) over standard F' plasmids is that they are more easily manipulated and more easily characterized and can be stably maintained without Cam selection in contrast to the assertion in the Invitrogen (Carlsbad, Calif.) and Stratagene (La Jolla, Calif.) product manuals, which state that Cam addition is necessary to maintain pACYC184-derived pLysS and pLysE.

Improved strains can be engineered from any bacterial host cell containing a T7 RNA polymerase that is inhibited by lysozyme expressed by a WT T7 lysozyme gene or T7 lysozyme mutant known in the art (K128Y etc). Examples of expression strains provided herein include *E. coli* strains ER301.1, ER301.2, ER3043, ER3044, ER3080, ER3081, ER3082 and ER3083. These strains were designed and constructed from ER2566 to optimize the ratio of T7 lysozyme to T7 RNA polymerase. Each carries either a WT T7 lysozyme gene or a mutant T7 lysozyme gene (lysY=K128Y). Additional expression strains including the fast growing strain C2984H (NEB catalog, Ipswich, Mass.) may be modified to contain T7 RNA polymerase inhibited by T7 lysozyme as described above.

An example of a suitable lysozyme mutant is the lysY gene which consists of a codon change (aag to tac) resulting in the variant protein K128Y that lacks amidase activity yet inhibits T7 RNA polymerase activity (Cheng at al., *Proc. Natl. Acad. Sci. USA* 91:4034-4038 (1994)).

Other examples of T7 lysozyme variants include those with a mutation selected from Y46F, K128Q, K128Y, K128M, K128W or K128I, all which also lack amidase activity, yet retain the ability to inhibit T7 RNA polymerase function (Chang et al., *Proc. Natl. Acad. USA* 91:4034-4038 (1994)). Other substitutions at positions 46 and 128 are expected to eliminate amidase activity without affecting polymerase inhibition.

The lysozyme variants described herein are demonstrated to be advantageous for loner membrane protein expression (FIG. 9). This can be measured in an assay that demonstrates the following factors:

(1) faster growth rate before and after induction;
(2) higher cell density achieved indicating less cell lysis; and
(3) at least 100-fold greeter viability than WT T7 lysozyme-expressing cells after the induction period indicating less cell lysis.

Using this assay, it was shown that ER3012 lysY/Iq snows improved tolerance to the expression of subunit b membrane protein as compared to pLysS and pLysE strains.

In an embodiment of the invention, improved yields of target protein can be obtained for toxic protein after induction. For example, FIG. 5 shows improved yields of subunit b using ER3012 lysY/lacIq. This strain grew more rapidly and reached the appropriate optical density for induction in 1.5 hrs less time, than several prior art strains, in particular BL21 (DE3) pLysS. Note that the subunit b expression plasmid (pAVD10) (source of pAVD10 (IMAXIO, Saint Beauzire, France) is lethal to BL21(DE3) upon transformation.

In another embodiment of the invention, transformed cells over-express the toxic subunit b membrane protein without making the cells susceptible to lysis. The current recommendation for T7 expression of extremely toxic protein is to employ a host cell carrying pLysE (Invitrogen Protein Expression manual, Carlsbad, Calif.). However, it is shown here that *E. coli* cells expressing wt T7 lysozyme from pLysE are more susceptible to lysis (FIG. 9). The culture density (OD600) of BL21(DE3) pLysE began to decrease within 2 hours of inducing subunit b expression.

The use of the non-lytic lysY variant to control T7 RNA polymerase function has particular utility for over-expressing other proteins of interest that are native, cell envelope proteins. We envisage further utility of lysY host cells for expression of heterologous proteins that are targeted to the inner or outer membrane or periplasmic space of *E. coli*. The over-expression and targeting of proteins to the cell envelope of *E. coli* imposes stress on the cell. For example, the Cpx envelope stress response is activated by aggregates of misfolded proteins at the periplasmic surface of the plasma membrane (Raivo *Mol. Microbiol.* 56:1119-1128 (2005)). Alteration in cell envelope composition (during protein over-expression) may also induce the Cpx response and result in increased susceptibility of the host to cell lysis.

While the use of T7 RNA polymerase for over-expression of target recombinant proteins is preferred, the co-expression of an active lysozyme is not advised in T7 protein expression strains where the protein of interest is targeted to the cell envelope. Even low levels of cell lysis in an expression culture will result in the detrimental release of lysozyme to the culture media.

In embodiments of the invention, the T7 expression hosts provided herein maintain a minimal basal level of T7 RNA polymerase and any un-induced polymerase is inactivated with the lowest effective level of T7 lysozyme. Hence, maximal T7 RNA pol-mediated protein expression occurs in a defined induction period.

The expression hosts described herein share the common property that the T7 RNA polymerase gene is located on the host cell chromosome. In addition, one or more of the following characteristics may define toe host cell.

(a) Expression of the T7 RNA polymerase is regulated by a lac operator/promoter and a LacI repressor.

(b) A multi-copy plasmid may be introduced into the host cell which contains a gene expressing the protein of interest under control of a T7 or T7-lac promoter. The multi-copy expression plasmid may further encode a lacI repressor. An example of a multi-copy expression plasmid is pET (Novagen, EMD Biosciences, Inc., Madison, Wis.).

(c) An F' plasmid is present in the host cell at a ratio of 1:1 with the host chromosome, in an example of a miniF plasmid described herein, a lysozyme gene is located on the plasmid under the control of a constitutive CAT promoter. The miniF plasmid optionally expresses lac repressor.

(d) A lysozyme gene and optionally a lacI or lacIq gene are inserted into the host chromosome. The lysozyme gene is constitutively expressed in the host cell.

(e) A substantial amount of chronic DNA damage can be tolerated by the host cell, for example, ER2566 can recover from DNA damage (sulA11) (Heitman et al., *Proc. Natl. Aced. Sci. USA* 86:2281-2285 (1989)); Lewis, *Micro. Mol. Biol. Rev.* 64:503-514 (2000)).

To assist in understanding the present embodiments of the invention, various terms have been described for use as the context allows.

"WT T7 lysozyme gene" is gene 3.5 from the bacteriophage T7 genome (Genbank accession no. NC_001604). The cloned fragment within pLysS and pLysE contains base pairs 10,665-11,296 of the T7 genome.

"pLysE" is a multi-copy pACYC184 plasmid containing the WT T7 lysozyme gene cloned into the BamHI site in the same orientation as the tetracycline promoter.

"pLysS" is a multi-copy pACYC184 plasmid containing the WT T7 lysozyme gene cloned into the BamHI Site in an orientation opposite to the tetracycline promoter, but in the same orientation to the cat promoter.

"pLysY" is a mufti-copy pACYC1841 plasmid containing the lysY gene cloned into the BamHI site in an orientation opposite to the tetracycline promoter, but in the same orientation to the cat promoter.

The "lysY gene" expresses the K128Y variant of T7 lysozyme. The gene name "lysY" refers to the open reading frame expressing the K128Y variant of T7 lysozyme regardless of the chromosomal or plasmid context of the gene.

The name "lysZ" is the WT T7 lysozyme gene within the context of a bacterial chromosome where lysozyme is expressed from the constitutive tet promoter.

"T7 expression strain" refers to a bacterial cell carrying a cloned copy of the bacteriophage T7 gene 1 encoding T7 RNA polymerase. The T7 gene 1 is typically controlled by an inducible promoter. The primary use of such strains is to express an mRNA of interest resulting in the expression of one or more proteins of interest.

"LacIq" refers to the lacI repressor gene expressed from a mutant lacI promoter resulting in over-expression of the Lac repressor protein. A wild-type *E. coli* cell generally contains only about ten copies of Lac repressor (Lehninger, Nelson and Cox; *Principles of Biochemistry* 2nd edition, p. 951. Worth Publishers, New York, N.Y. (1993)) "Toxic gene" refers to a gene where basal expression of the gene product exerts a growth defect on the host including a lethal effect to the host.

"Basal" refers to the non-induced level or repressed level of expression.

"Induction" refers to the act of adding inducer molecule or establishing conditions to initiate target gene expression.

"F' plasmid" refers to any vector having an origin of replication which is based on the ori2 replicon of the F "fertility" factor of *E. coli*. F' plasmid includes a single copy miniF plasmid (Hayakawa et al. *J. Bac.* 163(1):349-354 (1985)). In one example, the miniF plasmid is derived from the multi-copy pFOS1 (NEB 2005-06 catalog, page 314, Ipswich, Mass.).

"Amidase activity" of T7 lysozyme refers to the cleavage of the amide bond between N-acetyl-muramic acid and L-alanine within the peptidoglycan layer of bacterial cell walls (Cheng et al., *Proc. Natl. Acad. Sci. USA* 91:4034-4038 (1994); Inouye et al., *J. Biol. Chem.* 248: 7247-7252 (1973)).

"Competent cell" refers to a biological cell that is capable of acquiring foreign DNA such as a plasmid vector "LB" refers to a bacterial growth medium with the following composition per liter of water: 10 g Tryptone, 5 g yeast extract, 10 g sodium chloride, 1 g glucose, 1 g magnesium chloride-hexahydrate, adjusted to pH 7.2+/−0.1 with sodium hydroxide.

"SOB" refers to a bacterial growth medium with the following composition pre Liter of water 20g Tryptone, 5g yeast extract, 0.5 g sodium chloride, 2.5 mM potassium chloride, 10 mM magnesium chloride, adjusted to pH 7.0+/−0.1 with sodium hydroxide.

Strain Descriptions

ER2566 cries the T7 RNA polymerase gene inserted into the lac locus. Transcription of the T7 RNA polymerase gene is provided by a wild-type lacZ promoter.

ER2833 (U.S. Pat. No. 6,569,669) comes the T7 RNA polymerase gene inserted into the lac locus. Transcription of the T7 RNA polymerase gene is provided by a wild-type lacZ promoter. ER2833 contains an F' encoding a single copy of lacIq.

Strain Genotypes

ER2707 genotype: Δlac-169 robA1 creC510 hsdR514 endA recA1 ΔuidA::pir+.

ER2707=BW23473: pir+ strain used for propagation of pCD13PK5 and derivatives (Haldimann et al., *Proc. Natl. Acad. Sci. USA* 93:14361-14366. (1996)).

The following strains are derivatives of *E. coli* B. Unlike K-12, B is naturally deficient in Lon end dcm methylation; this is indicated by square brackets.

ER2566 genotype: fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 (NEB, Ipswich, Mass.)

ER2833 genotype: F' proA+B+lacIq zzf::Tn10 (TetR)/fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 (NEB, Ipswich Mass.)

BL21 genotype: hsdSB (rB-mB-) [Ion] ompT gal [dcm] (Invitrogen, Carlsbad, Calif.).

BL21(DE3) genotype: hsdSB (rB-mB-) [Ion] ompT gal [dcm] (DE3) (Invitrogen, Carlsbad, Calif.).

ER3011 genotype: fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 miniF-lysY (Cam$^R$).

ER3012 genotype: fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 miniF-lys-lacIq (Cam$^R$).

ER 3013 geneotype can be obtained from New England Biolabs, Inc., Ipswich, Mass.. ER3043 genotype: fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 attB::pCD13-lacIq-lysY (Spec$^R$)

ER3044 genotype: fhuA2 lacZ::T7 gene1 [Ion] ompT gal sulA11 R(mcr-73::miniTn10-TetS)2 [dcm] R(zgb-210::Tn10-TetS) endA1 Δ(mcrC-mrr)114::IS10 attB::pCD13-lacIq-lysS (Spec$^R$).

ER3080 genotype: fhuA2 lacZ::T7 gene1 [Ion] ompT gal attB::pCD13-lysY(Spec$^R$) sulA11 R(mcr-73::miniTn10-TetS)2 [dcm] R(zgb-210::Tn10-TetS) endA1 Δ(mcrC-mrr)114::IS10.

ER3081 genotype: fhuA2 lacZ::T7 gene1 [Ion] ompT gal attB::pCD13-lysY-lacIq (SpecR) sulA11 R(mcr-73::miniTn10-TetS)2 [dcm] R(zgb-210::Tn10-TetS) endA1 Δ(mcrC-mrr)114::IS10.

ER3082 genotype: fhuA2 lacZ::T7 gene1 [Ion] ompT gal attB::pCD13-lysZ (SpecR) sulA11 R(mcr-73::miniTn10-TetS)2 [dcm] R(zgb-210::Tn10-TetS) endA1 Δ(mcrC-mrr)114::IS10.

ER3083 genotype: fhuA2 lacZ::T7 gene1 [Ion] ompT gal attB::pCD13-lysZ-lacIq (SpecR) sulA11 R(mcr-73::miniTn10-TetS)2 [dcm] R(zgb-210::Tn10-TetS) endA1 Δ(mcrC-mrr)114::IS10.

All references cited herein, as we as provisional application Ser. No. 60/873,711 flied Dec. 8, 2006 and Ser. No. 60/959,322 filed Jul. 12, 2007, are incorporated by reference.

EXAMPLES

Example 1

Construction of miniF-lysY Plasmid

Figure 1:
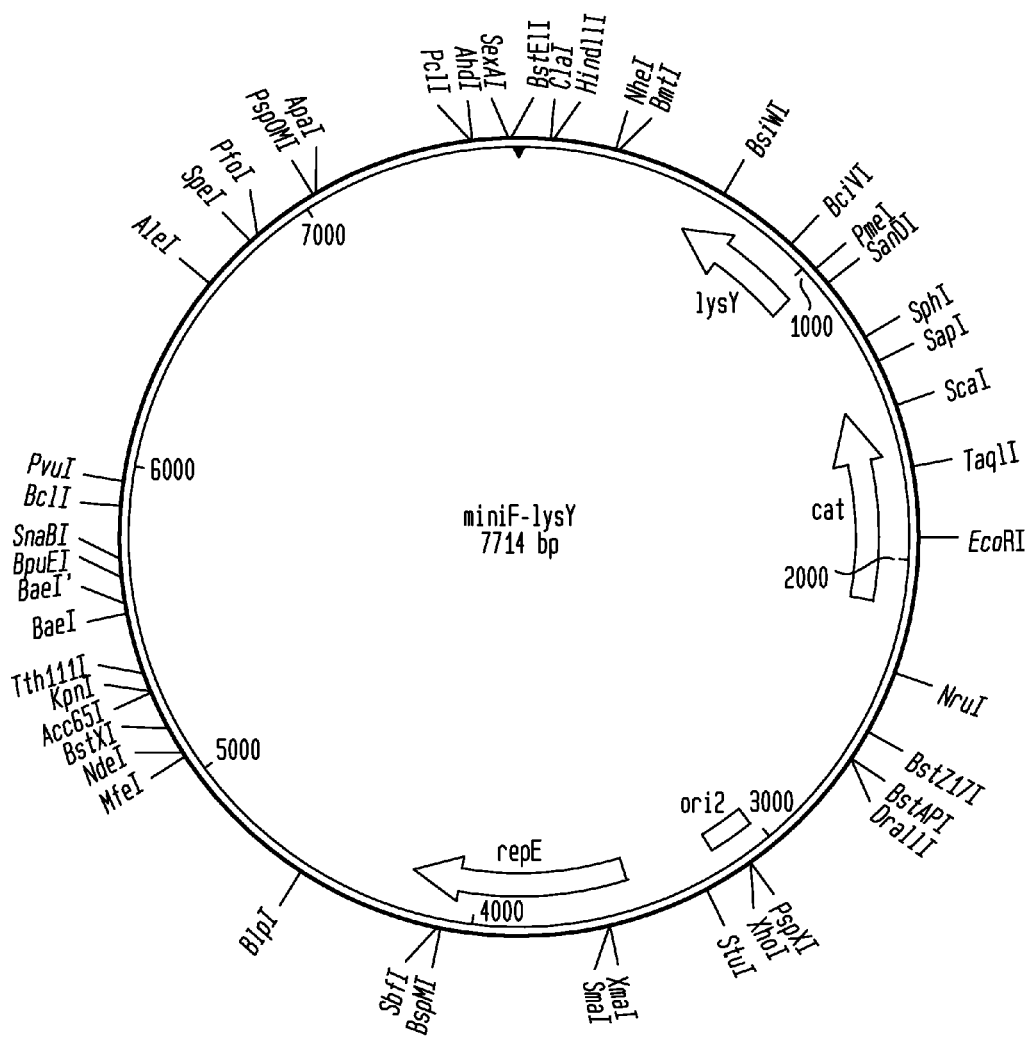
FIG. 1 shows a map of a single-copy vector, miniF-lysY, where LysY is constitutively expressed from the CAT promoter. The miniF vector is 7714 bp.
Figure 3:
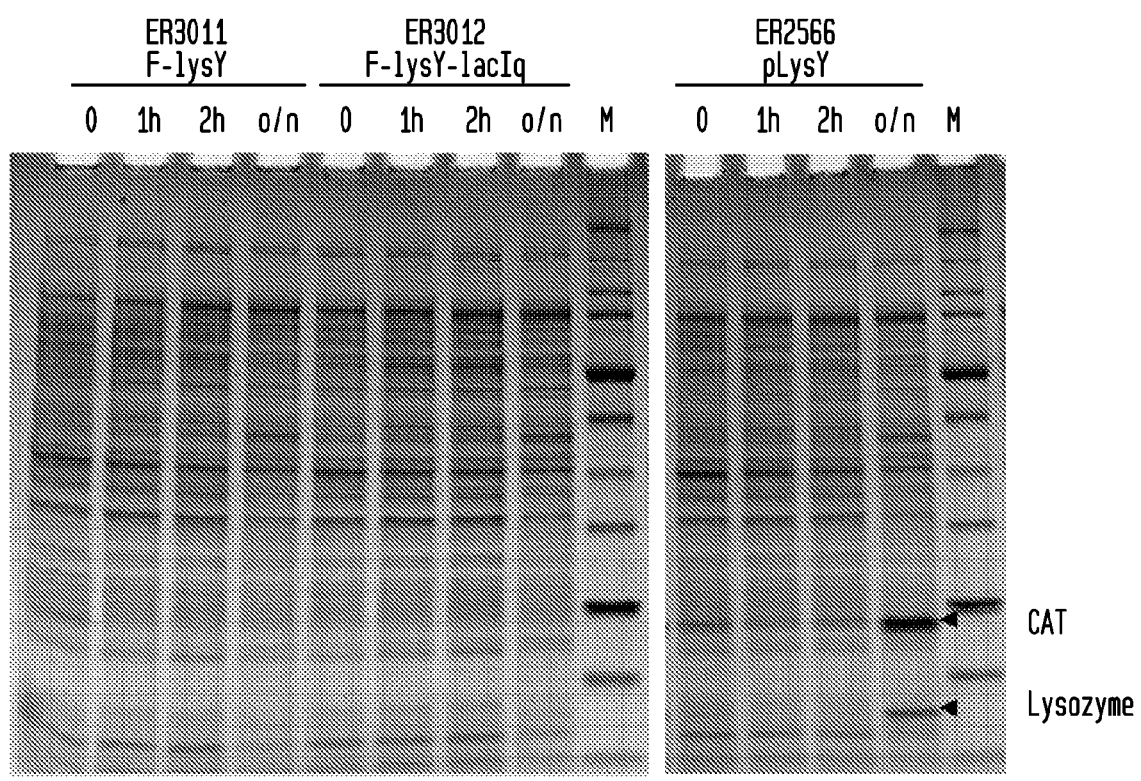
FIG. 3 shows SDS-PAGE analysis of single-copy (miniF-lysY) and multi-copy (pLysY) lysozyme expression in strains grown to saturation in LB media. Accumulation of lysozyme and CAT is evident in the multi-copy pLysY strain only as indicated by the arrows. F-lysY corresponds to miniF-lysY present in host cells identified as ER3011; F-lysY-lacIq corresponds to miniF-lysY-lacIq present in host cells identified as ER3012; M=NEB broad-range protein marker (New England Biolabs, Inc. (NEB), Ipswich, Mass.); CAT=25,663 daltons; lysozyme=17,014 daltons. The lanes are identified according to time of induction of the target gene prior to analysis (n hours).
Figure 4:
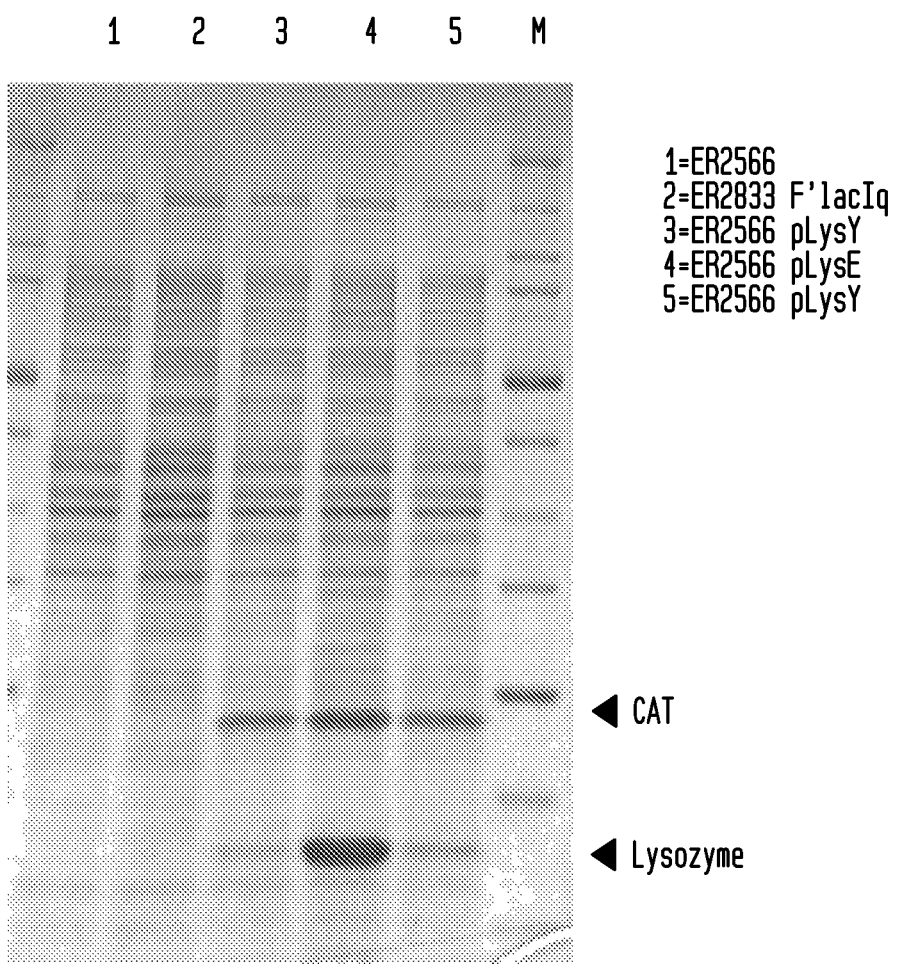
FIG. 4 shows a SOS-PAGE analysis of lysozyme and CAT expression in LB cultures grown 24 hours at 37° C. M=NEB broad-range protein marker. The host cells in the cultures are as follows: lane 1; ER2566, lane 2: ER2833 F'lacIq, lane 3: ER2566 pLysY; lane 4: ER2566 pLysE end lane ER2566 pLysY.

The plasmid miniF-lysY is a single-copy plasmid derived from pFOS1 (FIG. 1). The lysY gene was excised from a pACYC184 construct (pLysY) using SalI and SspI. This 1358bp fragment was ligated into pFOS1 prepared by SalI-HpaI digestion and treatment with Antarctic phosphatase (NEB, Ipswich, Mass.). The ligation reaction was transformed into ER2566 and the transformants were selected on LB agar plates containing 30 μg/mL CAM. The miniF plasmid of transformant 2566-1B was confirmed to be pFOS1 encoding the lysY insert. In the miniF-lysY plasmid, the lysY gene is present just downstream of the cat gene in the same orientation as the CAT gene. This configuration allows for read-through transcription from the CAT promoter to provide transcripts of the lysY gene. This is similar to the context of the lysozyme gene in the multi-copy plasmid pLysS which is maintained at about 15 copies per cell. Due to the difference in copy number from pLysS to the miniF plasmid, the expression level of lysozyme protein may be reduced as much as 15-fold. In fact, lysozyme and CAT are not observed by SDS-PAGE after overnight growth of ER3011 or ER3012 (FIG. 3), whereas prominent bands of both proteins are routinely observed when using strains carrying pLysY or pLysE (FIGS. 3 and 4). Especially in the case of pLysE, unnecessary cellular resources are wasted in the production of lysozyme and the CAT gene product.

Example 2

Construction of miniF-lysY-lacIq Plasmid

Figure 2:
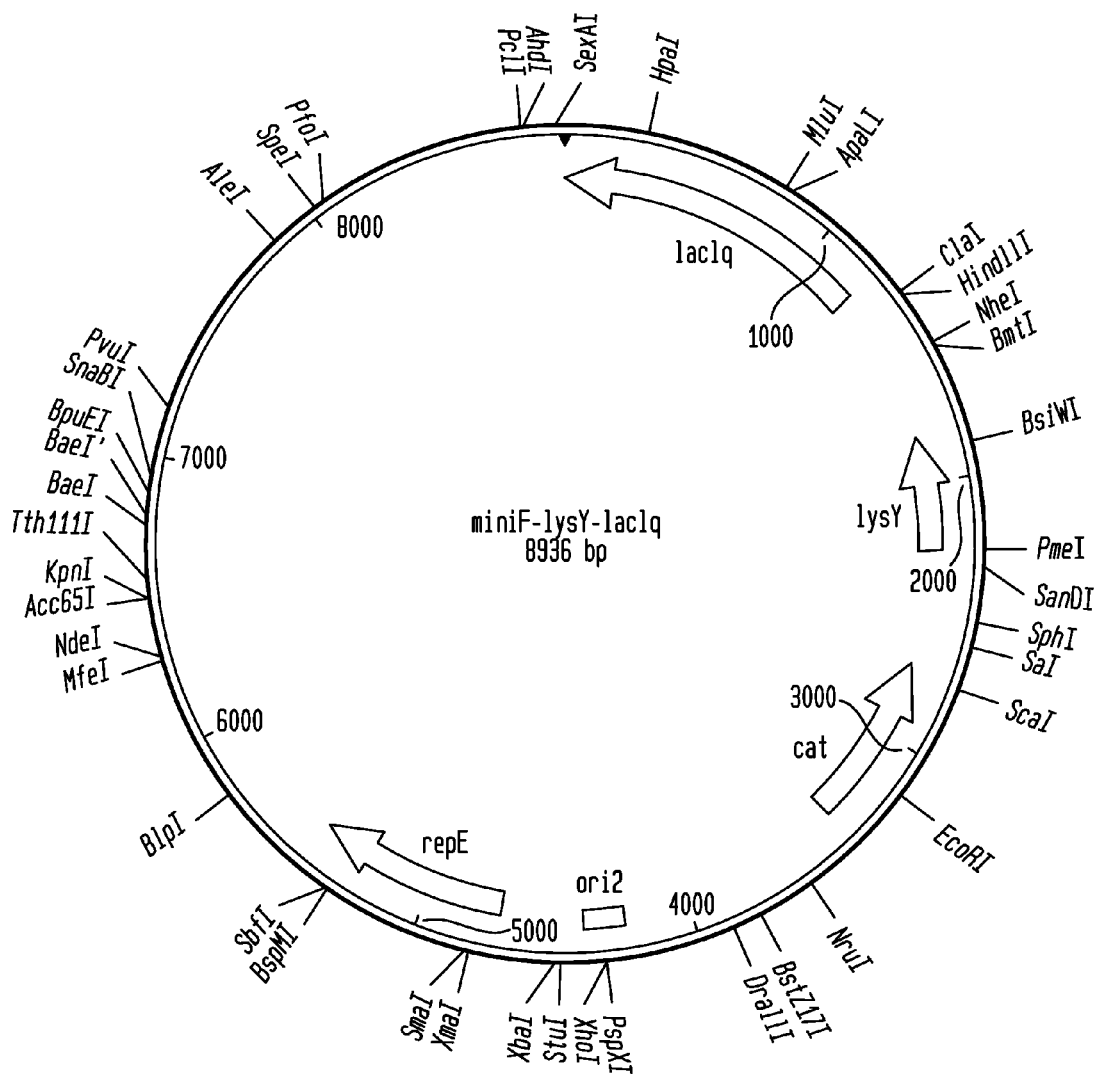
FIG. 2 shows a map of single-copy vector, miniF-lysY-lacIq. The miniF vector is 8936 bp and includes lacIq in addition to the lysY gene which is constitutively expressed from the CAT promoter.

The plasmid miniF-lysY-lacIq is a single-copy plasmid derived from pFOS1 (FIG. 2). This plasmid was constructed as follows: First the lacIq gene (ZraI-digested blunt-end fragment) was inserted into pLysY. This was achieved by ligation of the lacIq fragment into the blunt-filled XbaI site of the pLysY plasmid.

Forward PCR primer for creation of the lacIq gene from the lacI gene:

```
                                       (SEQ ID NO: 1)
5'-CCACCAGACGTCACCATCGAATGGTGCAAAACCTTTCG-3
```

The ZraI restriction site is underlined and the lacIq promoter mutation is bolded.

Reverse primer for lacIq PCR amplification:

```
                                       (SEQ ID NO: 2)
5'-ATGATAAGACGTCAAACATGAGAATTGTGCC-3'
``` the restriction site is underlined.

Plasmid dunes were screened to identify those with lacIq transcription in the opposite orientation from the lysY gene so that lysozyme expression would be unaffected. (ZraI is a restriction endonuclease obtained from NEB, Ipswich, Mass.). Next, the 2588 bp lysY-lacIq fragment was excised with SalI and SspI and ligated into pFOS1 prepared by SalI-HpaI digestion and treatment with Antarctic phosphatase (NEB, Ipswich, Mass.). The ligation reaction was transformed into ER2566 and the transformants were selected on LB agar plates containing 30 μg/mL CAM. The miniF plasmid of transformant 2566-2E was confirmed to be pFOS1 encoding the lysY-lacIq insert. In the plasmid miniF-lysY-lacIq, the lysY and lacIq genes are present downstream of the CAT gene in the same orientation as the AT gene. This configuration allows for read-through transcription from the CAT promoter to provide transcripts of the lysY gene. This is similar to the context of the lysozyme gene in the multi-copy plasmid pLysS which is maintained at about 15 copies per cell. Due to the difference in copy number from pLysS to the miniF plasmid, the expression level of lysozyme protein may be reduced as much as 15-fold. In fact, lysozyme and CAT are not observed by SDS-PAGE after overnight growth of ER3011 or ER3012 (FIG. 3), whereas prominent bands of both proteins are routinely observed when using strains carrying pLysY or pLysE (FIGS. 3 and 4). Especially in the case of pLysE, unnecessary cellular resources are wasted in the production of lysozyme and the CAT gene product.

Example 3

Construction of a Host Strain Carrying miniF-lysY

The miniF-lysY plasmid present in transformant 2566-1B may be introduced into a T7 expression strain (lacking F') to reduce the basal level of T7 pol-mediated transcription. As ER2566 is a preferred T7 expression host, transformant 2566-1B described in Example 1 was designated ER3011 (miniF-lysY).

Example 4

Construction of a Host Strain Containing miniF-lysY-lacIq

The miniF-lysY-lacIq plasmid present in transformant 2566-2E may be introduced into a T7 expression strain (lacking F') to reduce the basal level of T7 pol-mediated transcription. As ER2566 is a preferred T7 expression host, transformant 2566-2E described in Example 2 was designated ER3012 (miniF-lysY-lacIq).

Example 5

Expression of Toxic Protein Subunit b

Strains ER3011 and ER3012 were used as host strains to express the toxic proteins ATP synthase subunit b (FIG. 5). ER3012 lysY/lacIq provides the highest ratio of induced (+) to uninduced (−) protein level. As the expression of subunit b is known to generally affect host cell growth, the growth rate without inducer is an effective measure of the basal T7 expression level. ER3012 exhibited the highest growth rate in LB media before induction when carrying the toxic subunit b plasmid pAVD10 (FIG. 6). All cultures were induced within the OD600 range of 0.66 to 0.92. ER3012 achieved this point of induction 1.5 hours earlier than the other strains in the experiment. Thus, we conclude that the combination of lysozyme with lacIq expression resulted in the lowest basal T7 polymerase function. The next most effective means to minimize T7 expression is the expression of lysozyme alone. The least effective host modification was exemplified by ER3013 which contained a copy of the lacIq gene and not the lysozyme gene. Most striking is that a single copy of a lysozyme gene was adequate to counteract the basal level of T7 RNA polymerase in the parent ER2556. This finding is counterintuitive to current recommendations by those skilled in the art. When using BL21(DE3), excessive expression of lysozyme was previously suggested as the best method for toxic gene expression (Invitrogen product manual, Carlsbad, Calif.).

Example 6

Expression of Uracil DNA Glycosylase

The results obtained when the target gene was UDG were similar to those for subunit b (FIG. 7). In this analysis, BL21 (DE3) was included as a control. The common phenomenon of excessive basal T7 expression in this control strain was observed with UDG. The UDG gene is carried by pTYB11, a multi-copy plasmid designed for controlled expression as it carries the lad gene and encodes a T7-lac promoter (NEB 2005-06 catalog, p. 332, Ipswich, Mass.).

Example 7

Construction of Host Strains ER3043 and ER3044 Containing a Single Copy of a Lysozyme and a lacIq Gene on the Chromosome ER3043 and ER3044 were each derived from ER2566 and each was modified at the lambda attachment site (attB chromosomal locus). Specific and stable DNA integration at attB was achieved using the genetic system described by Platt et al., *Plasmid* 43:12-23 (2000). (Platt et al. describe pPICK and PCD13PKS, Integration primer B, and pir). Preferential integration at attB occurs even when the integration construct pCD13PKS carries an endogenous *E. coli* gene (Samuelson et al., *Nature* 406: 637-641 (2000)).

ER3043 expresses the lac repressor and the lysozyme variant K128Y from the chromosome. This was accomplished as follows: First, the parent ER2566 was transformed at 30° C. with pPICK. Next, pCD13PKS-lacIq-lysY was introduced by transformation at 30° C. and selection on LB-agar containing 20 µg/mL kanamycin and 25 µg/mL spectinomycin. Then attB integrants were isolated by a series of three streaks at 42° C. on LB-agar plates containing 25 µg/mL spectinomycin, ER3043 contains the integrated construct pCD13PKS-lacIq-lysY (see FIG. 8). In this construct, the lysY gene is downstream of the lacIq gene and transcription of both genes is initiated at the lacIq promoter. To obtain this configuration, the ZraI lacIq fragment was ligated into the Klenow-filled SalI site of pACYC184-lysY. Next, the lacIq-lysY fragment was isolated by EagI-digestion and Klenow followed by HindIII digestion. This two-gene fragment was ligated into pCD13PKS prepared by SapI-digestion and fill-in followed by HindIII-digestion. The SapI-HindIII deletion removes the lac operator/promoter region of pCD13PKS so the constitutive lacIq promoter is the only determinant in the expression of lac repressor and lysozyme K128Y.

Proper attB integration of pCD13PKS-lacIq-lysY was verified by using the PCB primers A-D as described in Platt at al., *Plasmid* 43: 12-23 (2000). However, primer D was redesigned to anneal downstream of the SapI site (a shift of 8 bp).

NEB (Ipswich, MA) primer D:
5'-GCTTCCTCGCTCACTGACTC-3'.     (SEQ ID NO: 3)

Primer pair A/B did not give a product indicating that the attB site is occupied. Primer pair A/C gave a 0.6 kb product indicating correct integration at attB. Primer pair B/D gave a 1.1 kb product indicating correct integration at attB. Primer pair C/D did not give a 1.5 kb product indicating single-copy integration.

ER3044 expresses lac repressor and WT lysozyme from the chromosome. The construction of ER3044 was carried out exactly as described for ER3043 beginning with pLysS rather than pLysY. The ZraI lacIq fragment was ligated into the SalI-filled site of pLysS and in the same orientation as the lysozyme gene. The integration of pCD13PKS-lacIq-lysS at attB is identical to the diagram of FIG. 8. Proper, single-copy attB integration within ER3044 was verified by using the PCR primer pairs described above.

The attB inserts of both ER3043 and ER3044 were PCR-amplified to confirm the lacIq and lys gene sequences. M13mp18 sequencing primer #S1224S (NEB, Ipswich, Mass.) anneals to a sequence adjacent to the pCD13PKS polylinker and integration primer B anneals to a sequence within the *E. coli* chromosome flanking the attB site PCR amplification of genomic DNA using #S1224S and primer B gave the expected 4 kb fragment for both strains. The lacIq gene within each fragment was verified using sequencing primers #S1208S and #S1209S (NEB, Ipswich, Mass.). The lysozyme gene within each fragment was verified using sequencing primers #S1219S and #S1223S (NEB, Ipswich, Mass.). Furthermore, methylene chloride-induced cell lysis was verified for ER3044. Addition of 2 drops of methylene chloride to 0.2 mL cell culture induced visible cell lysis within 3 minutes. Strains expressing lysozyme variant K128Y did not undergo lysis in this test. The expression level of lysozyme variant K128Y in ER3043 was expected to be identical to lysozyme expression in ER3044. Strains ER3043 and ER3044 were resistant to 25 μg/mL spectinomycin. This attB integration marker does not interfere with the propagation of any of the commonly used plasmid vectors.

Example 8

Construction of Host Strains Containing a Single Chromosomal Copy of a T7 Lysozyme Gene where Expression is from the Tetracycline Promoter ER3080, ER3081, ER3082 and ER3083 were each derived from ER2566 and each was modified at the attB chromosomal locus (FIGS. 10a and 10b). Specific and stable DNA integration at attB was achieved using the genetic system described by Platt at al., Plasmid 43:12-23 (2000) and described in Example 7. ER3080 expresses the T7 lysozyme variant K128Y from the integrated plasmid pCD13-lysY. ER3081 expresses T7 lysozyme variant K128Y and the lac repressor from the integrated plasmid pCD13-lysY-lacIq. ER3082 expresses WT 17 lysozyme (lysZ) from the integrated plasmid pCD13-lysZ. ER3083 expresses WT T7 lysozyme (lysZ) and the lac repressor from the integrated plasmid pCD13-lysZ-lacIq.

The construction of these our strains was accomplished in the blowing manner: First, pLysE was digested with XbaI and filled with Klenow to create a blunt end. The lacIq gene (ZraI fragment) was ligated into the filled XbaI site and plasmid cones were screened to isolate a clone where transcription of lacIq is opposite to transcription from the tet promoter. This strategy was chosen so that lysozyme gene transcription would be unaffected. The modified pLysE construct was named pLysE-lacIq. The SspI-EagI fragment from pLysE and pLysE-lacIq was transferred to pCD13PKS, prepared by SapI-digestion and fill-in followed by NotI-digestion. The SapI-NotI deletion removes the lac operator/promoter region of pCD13PKS so that lysozyme gene expression is driven only by the constitutive tot promoter. The pCD13 derivatives expressing WT lysozyme were named pCD13-lysE1 and pCD13-lysEIQ1. The corresponding lysY constructs were created from pCD13-lysE1 and pCD13-lysEIQ1 by BamHI-digestion and replacement of the WT lysozyme gene with the lysY gene. The lysY gene was isolated by BamHI digestion of pLysY. Multiple lysY ligation clones were screened by PmeI-SacII digestion to identify clones where the lysY gene recombined in the same orientation as transcription from the tet promoter. Two such clones were named pCD13-lysY1 and pCD13-lysYIQ3. In a four pCD13PKS derivatives, lysozyme gene expression is thus expected to be similar.

After single-copy chromosomal integration of any of these four pCD13PKS derivatives, the expression of lysozyme is expected to be at least 15-fold reduced compared to the expression of lysozyme in strains carrying pLysE as this pACYC184 derivative is maintained at approximately 15 copies per cell.

Each of the four pCD13PKS derivatives was transformed into ER2566 carrying pPICK. The transformation mixes were plated on LB-agar containing 25 μg/mL spectinomycin and 20 μg/mL kanamycin to establish replication of the pCD13 constructs. Then each established strain was streaked 3 times at 42° C. on LB-agar containing 25 μg/mL spectinomycin to select for attB integration.

Proper attB integration of pCD13 constructs was verified by using the PCR primers A-D as described in Example 7. The attB insertion of four positive strains was amplified by PCR using primers s1224s and primer B. Note that s1224s anneals to the pCD13PKS plasmid sequence while primer B anneals to the E. coli chromosome. The lysozyme gene sequence within each attB insertion was verified using sequencing primers s1319s and s1223s. After sequence verification, the four strains of interest were entered into the NEB (Ipswich, Mass.) strain library and given the names ER3080, ER3081, ER3082 and ER3083. The genotypes of the four strains reflect the following simplified names of the integrated plasmids:

ER3080: pCD13-lysY=pCD13-lysY1.
ER3081: pCD13-lysY-lacIq=pCD13-YIQ3
ER3082: pCD13-lysZ=pCD13-lysE1
ER3083: pCD13-lysZ-lacIq=pCD13-EIQ1

Example 9

Expression of Toxic Protein Subunit b in Host Strains Containing a Single Chromosomal Copy of a T7 Lysozyme Gene The four chromosomal lysozyme strains ER3080-ER3083 were transformed with pAVD10 and plated on LB-agar containing 100 μg/mL Amp. A direct comparison Was made to the preferred miniF strain ER3012 lysY/Iq. Overnight cultures were inoculated (1:100) into fresh 10 mL LB-Amp for evaluation of growth rate and expression of subunit b. FIG. 11 displays the favorable growth rates of all cultures grown simultaneously at 37° C. The chromosomal lysY strains outperformed the equivalent lysZ strains in this experiment again indicating the advantage of using a lysozyme variant lacking activity when the target protein is a membrane protein. The chromosomal lysY/Iq strain ER3081 displayed a growth rate nearly identical to the miniF lysY/Iq strains ER3012. FIG. 12 displays the subunit b expression profile of all 5 strains described in FIG. 11. Each strain produced subunit b at a high level and, in every case, a favorable ratio of induced protein to non-induced protein was observed (at least 10-fold). The level of lysozyme expression appears to be similar as measured by the basal subunit B expression (see FIG. 12). All five strains described in FIGS. 11 and 12 are preferred for the controlled T7 expression of toxic proteins. The four plasmid-free strains (ER3080, ER3081, ER3082 and ER3083) are the most useful as they lack any commonly used antibiotic selection marker. Note that Spectinomycin selection is not necessary to maintain the integrated pCD13PKS plasmids.

The invention claimed is:

1. A genetically engineered host cell capable of expressing a toxic protein, the host cell, comprising:
   (a) a chromosome in which is contained one or more T7 RNA polymerase genes; and
   (b) one or more genes encoding a T7 RNA polymerase inhibitor located in an F' plasmid or on the chromosome.

2. The host cell according to claim 1, wherein the one or more T7 RNA polymerase genes are present in a ratio of 1:1 with the one or more T7 RNA polymerase inhibitor genes.

3. The host cell according to claim 1, further comprising: a gene expressing LacI or LacIq.

4. The host cell according to claim 1, wherein the T7 RNA polymerase inhibitor gene is the T7 lysozyme gene.

5. The host cell according to claim 4, wherein the T7 lysozyme gene expresses a mutant T7 lysozyme.

6. The host cell according to claim 4, wherein the mutant T7 lysozyme has a mutation selected from Y46F, K128Q, K128Y, K128M, K128W and K128I.

7. The host cell according to claim 1, wherein the cell is competent for receiving foreign DNA.

8. The host cell according to claim 2, wherein the cell is an *E. coli* cell.

9. An F' plasmid, comprising: a wild type T7 lysozyme gene or a mutant thereof capable of expressing a T7 lysozyme protein wherein the protein expressed by the mutant gene is characterized by a mutation at position Y46 or K128, the wild type or mutant gene being operably linked to a constitutive promoter.

10. The F' plasmid according to claim 9, wherein the T7 lysozyme mutant gene expresses a protein having a mutation selected from Y46F, K128Q, K128Y, K128M, K128W and K128I.

11. A method, comprising the steps of:
   (a) providing a genetically engineered host cell according to claim 1;
   (b) transforming the host cell with a plasmid containing a target gene;
   (c) incubating the host cell to a cell density sufficient to permit expression of the target gene; and
   (d) inhibiting T7 RNA polymerase activity until initiation of induction so as to permit expression of the target gene in the genetically engineered host cell.

12. A method according to claim 11, wherein the target gene expresses a toxic protein.

13. A method according to claim 11, wherein the toxic gene product is a membrane protein.

14. A method according to claim 11, wherein the T7 RNA polymerase inhibitor is selected from a wild type T7 lysozyme gene, LysY or mutants thereof.

15. A method according to claim 14, wherein the mutant T7 lysozyme gene expresses a protein having a mutation selected from Y46F, K128Q, K128Y, K128M, K128W and K128I.

16. An F'plasmid according to claim 9, inserted into a genetically engineered host cell capable of expressing a toxic protein, and containing a chromosome in which is contained one or more of the T7 RNA polymerase genes.

* * * * *